United States Patent [19]

Jordan

[11] 4,450,104

[45] May 22, 1984

[54] WATER INSOLUBLE GEL MATRIX CONTAINING LECTIN BOUND TO ANTITHROMBIN

[75] Inventor: Robert E. Jordan, Concord, Calif.

[73] Assignee: Cutter Laboratories, Inc., Berkeley, Calif.

[21] Appl. No.: 426,560

[22] Filed: Sep. 29, 1982

Related U.S. Application Data

[62] Division of Ser. No. 192,286, Sep. 30, 1980, Pat. No. 4,386,025.

[51] Int. Cl.³ ..................... C07G 7/00; A61K 31/725
[52] U.S. Cl. ............................. 260/112 B; 260/112 R
[58] Field of Search ........................ 260/112 R, 112 B

[56] References Cited

U.S. PATENT DOCUMENTS

| | | | |
|---|---|---|---|
| 4,119,774 | 10/1978 | Andersson et al. | 536/21 |
| 4,289,747 | 9/1981 | Chu | 435/7 X |
| 4,301,153 | 11/1981 | Rosenberg | 424/101 X |
| 4,371,515 | 2/1983 | Chu | 260/112 R X |

OTHER PUBLICATIONS

Febs Letters, vol. 29, No. 2, 1973, pp. 185-188, Hayman et al.
Biochemistry, vol. 16, No. 9, 1977, pp. 1787-1794, Lotan et al.
Nature New Biology, vol. 236, 1972, pp. 23-25, Allan et al.
J. of Biol. Chem. vol. 254, No. 10, 1979, pp. 4000-4008, B. Havanandan et al.
Exp. Cell Research 109, 1977, pp. 95-103, Pearlstein.
J. of Biol. Chem. vol. 254, No. 7, pp. 2400-2407, 1979, Baenziger et al.
J. of Biol. Chem. vol. 254, No. 7, pp. 8740-8743, 1979, Nexo et al.
Analytical Biochemistry, 115, pp. 130-137, 1981, Dorai et al.

*Primary Examiner*—Howard E. Schain
*Attorney, Agent, or Firm*—Lester E. Johnson; Theodore J. Leitereg

[57] ABSTRACT

A lectin-containing, water-insoluble gel matrix with a glycoprotein reversibly bound thereto can be used for fractionating a polysaccharidic substance capable of being separated into components of differing activity by virtue of differing affinity for the glycoprotein. In this manner, heparin can be fractionated into high activity and low activity components.

5 Claims, No Drawings

WATER INSOLUBLE GEL MATRIX CONTAINING LECTIN BOUND TO ANTITHROMBIN

This application is a division of application Ser. No. 192,286, filed Sept. 30, 1980, now U.S. Pat. No. 4,386,025.

BACKGROUND OF THE INVENTION

1. Field of the Invention

This invention relates to and has among its objects the provision of novel methods for fractionating polysaccharidic substances into components of differing activity. It is a particular object of the invention to prepare high activity heparin in large quantities using a novel lectin-containing, water-insoluble gel matrix to which antithrombin and heparin are applied. Further objects of the invention will be evident from the following description wherein parts and percentages are by weight unless specified otherwise.

2. Description of the Prior Art

Heparin is a glycosaminoglycan, having uronic acid, glucosamine, and sulfate moieties, that functions as a blood anticoagulant by binding to the inhibitor antithrombin and accelerating the rate at which this inhibitor neutralizes serine proteases of the coagulation mechanism.

The injection of unfractionated heparin alone (either intravenously or subcutaneously) is routinely employed for the treatment of thromboembolism or for the prevention of clot formation in at-risk patients. Despite its widespread and growing use for these purposes, problems concerning side effects and efficacy have been pointed out. Some of the problems associated with current anticoagulant therapy are the following:

(1) Patients often demonstrate widely different dose responses to administered heparin. This requires a rather individualized treatment procedure and constant monitoring of the resulting clotting characteristics. Quite often, the desired dosage is exceeded which necessitates the neutralization of the excess heparin.

(2) Heparin, as it is used clinically, is approximately 30% active as an anticoagulant (as defined by its ability to interact with antithrombin which results in the rapid inhibition of thrombin and other coagulation proteases). The majority of administered heparin (70%) shows no particular affinity for antithrombin but can interact with many other plasma proteins with consequences that may be undesirable. The best example of this phenomenon is the activation of lipoprotein lipase which results in the clearance of circulating triglyceride.

(3) Heparin is a highly charged polyanion and is capable of many non-specific electrostatic interactions with plasma proteins, blood cells, and endothelial surfaces. Upon injection heparin becomes distributed among these components. Although antithrombin binds in a specific fashion and with high affinity to the active fraction of the total heparin, is is unlikely that all of the anticoagulant heparin binds to the plasma antithrombin. Thus, the actual anticoagulant dosage of heparin received during heparin therapy is a complex function of any number of equilibria which reduce the amount of productive heparin-antithrombin complexes formed.

(4) Heparin has been implicated as a cause of thrombocytopenia due to its interaction with platelets in patients undergoing prolonged anticoagulant therapy.

(5) Circulating antithrombin levels have been shown to decrease as a result of prolonged administration of heparin. Antithrombin levels lowered in this way are reported to remain depressed for several days following the end of treatment. This may be a particularly undesirable effect in patients predisposed to thrombosis.

(6) In patients with congenital antithrombin deficiency, the administration of heparin may not be completely efficacious.

The administration of antithrombin has also been proposed to be a means of controlling undesirable clot-formation in at-risk patients. Those who might benefit most from this therapy would be those congenitally deficient in antithrombin as well as individuals undergoing certain types of surgery. In order for this type of therapy to be effective, however, very large amounts of antithrombin would be required. Also, treatment of congenital antithrombin deficients with antithrombin concentrates would require large amounts of this protein at frequent dosages since the plasma half-life of antithrombin is about three days.

Fractionation of heparin into high and low activity components is difficult because heparin species possessing active chain sequences are virtually indistinguishable from those possessing inactive chains. However, heparin has been separated into high activity and low activity components by sucrose density gradient centrifugation of heparin mixed with antithrombin-heparin cofactor (Lam et al, *Biochemical and Biophysical Research Communications*, 1976, Vol. 69, No. 2, pages 570–577). Heparin also has been fractionated by affinity chromatography on immobilized antithrombin (Höök et al, *FEBS Letters*, 1976, Vol. 66, pages 90–93. In this method antithrombin is coupled covalently with a cyanogen bromide-activated, water-insoluble matrix, such as, for example, Sephadex ®, Sepharose ®, etc. Heparin is applied to the immobilized antithrombin material, which adsorbs the high-activity heparin species. After separation of the matrix containing the adsorbed high activity component from the low activity heparin component, the matrix is treated with a high salt medium to elute the high activity heparin species therefrom.

An alternative method involves the separation of heparin-antithrombin complexes from unbound heparin by gel chromatography on Sephadex ® G100. However, due to the size heterogeneity inherent in commercial heparin preparations and the resulting broad chromatographic profile of the heparin itself, the above method must employ heparin fractions of defined molecular weight in order to permit the separation of the heparin-antithrombin complex. This has been accomplished with a low molecular weight heparin species having an average molecular weight of 6000 daltons (Rosenberg et al, *Proc. Nat. Acad. Sci.*, 1978, Vol. 75, No. 7, pages 3065–3069). In this case, a heparin-antithrombin complex was separated from free heparin in an initial gel chromatographic step and was subjected to a second chromatography in the presence of high salt to disrupt the complex. The high affinity heparin obtained in this sequence had a specific anticoagulant activity of about 360 units/mg compared to the starting pool of 96 units/mg. A low affinity heparin pool of 4 units/mg was also obtained by repetitive depletion of the starting material.

A complex of antithrombin and high molecular weight, high affinity heparin was also prepared by gel chromatography on Sephadex ® G100 (Rosenberg et al, *B.B.R.C.*, 1979, Vol. 86, No. 4, pages 1319–1324). In this instance, the complex was separated from excess antithrombin for the purpose of analytical characterization of the ratios contained and required the use of a heparin species previously fractionated both for size and activity.

One major problem confronting workers in all of the above-described methods is that the fractionation or preparation has been accomplished only on a laboratory scale. In other words, large scale manufacture or manufacture of pharmaceutically useful amounts has not been realized either because of limitations inherent in the method or because of the limited availability of antithrombin.

Fractionation of heparin into high and low activity components is complicated further by the fact that antithrombin coupled to a water-insoluble matrix cannot be recovered without substantial or total destruction of the antithrombin. This results because the antithrombin is covalently bound to the matrix by means of, for example, a cyanogen bromide coupling process, and the conditions necessary to cleave the coupling destroy the antithrombin.

Recently, a new method for the measurement of the binding of ligands to solubilized membrane receptors, such as a receptor for epidermal growth factor-urogastrone (EGF-URO) was described by Nexo et al, *J. Biol. Chem.*, 1979, Vol. 254, No. 18, pages 8740–8743. The soluble receptor is first immobilized on lectin-agarose beads and ligand binding is then determined on the bead-bound receptor. The chromatographic and binding properties of solubilized receptor can be studied due to the restoration of the ligand recognition property of the receptor. After the solubilized receptor is immobilized on lectin agarose, the binding of a ligand, such as EGF-URO, to the immobilized receptor is rapid, reversible, peptide specific, and of high affinity. The author notes that his method deserves consideration for the study of any receptor that recognizes a ligand free of carbohydrate.

SUMMARY OF THE INVENTION

I have found that polysaccharidic material composed of both high and low activity components can be separated into its components of differing activity by fractionation on a lectin-containing, water-insoluble matrix having reversibly bound thereto a glycoprotein specific for gradiently binding the components of differing activity which comprise the material to be fractionated. The components of polysaccharidic material having differing activities can be removed from the matrix by gradient elution.

The invention described herein further provides means for obviating the above problems with respect to heparin fractionation. In the method of the invention antithrombin can be reversibly coupled to a novel lectin-containing, water-insoluble gel matrix in a reversible, i.e., nondestructively-removable, fashion; and the heparin to be fractionated is contacted therewith. The high activity heparin component is adsorbed on the matrix leaving the low activity heparin component to be separated easily therefrom, for example, by selective elution. Then, the high activity heparin component is eluted from the matrix. It is a special feature of the invention that antithrombin may be removed easily and nondestructively from the matrix in high yield once the fractionation of heparin has been completed or the matrix with reversibly bound antithrombin may be used repeatedly to fractionate heparin.

Another advantage of the invention is that valuable antithrombin is not lost as a consequence of the fractionation of heparin. As mentioned above, in the known methods antithrombin is covalently bound to a matrix and cannot be removed without destroying it. In the instant case the antithrombin is readily removable from the matrix, if so desired, because it is not bound covalently thereto; thus, antithrombin may be non-destructively removed from the matrix and used for other purposes.

Another advantage of the invention in the fractionation of heparin is its ease of application. Once the lectin-containing, water-insoluble gel matrix with antithrombin immobilized thereon is prepared, unfractionated heparin merely is applied to the matrix. Selective elution of the matrix yields fractionated heparin, i.e., the low activity heparin component (LAH) and the high activity heparin component (HAH).

DESCRIPTION OF THE PREFERRED EMBODIMENTS

In the following description emphasis is directed to the fractionation of heparin using a novel lectin-containing, water-insoluble matrix. In its broad ambit the invention can be applied to the fractionation of all types of non-lectin binding, polysaccharidic substances, particularly, mucopolysaccharidic substances, capable of being separated into components of differing biological activity by virtue of differing affinity for a glycoprotein using a particular novel lectin-containing matrix having reversibly bound thereto the glycoprotein specific for gradiently binding the polysaccharidic material to be fractionated. By the term "polysaccharidic" is meant that the material contains polysaccharide or carbohydrate moieties or residues; the term "mucopolysaccharidic" defines a material which generally contains both polysaccharide and sulfate or carboxylic moieties or residues. By the term "gradient binding" is meant that the components of differing activity which comprise the material to be fractionated exhibit graded differences in affinity towards the glycoprotein reversibly bound to the matrix. In general, the glycoprotein should contain a carbohydrate residue. Human antithrombin has been found to contain covalently linked N-acetylglucosamine, mannose, galactose, and sialic acid (Danishefsky et al, *J. Biol. Chem.*, 1978, Vol 253, No. 1, pages 32–37).

As mentioned above, in the method of the invention antithrombin is reversibly immobilized on a lectin-containing, water-insoluble matrix by means of interaction between antithrombin and the lectin. The lectin-containing, water-insoluble matrix is prepared from a water-insoluble polymeric material and a lectin. As the water-insoluble polymeric material one may use any material to which the lectin can be bound; thus, one may use, by way of example and not limitation, certain cross-linked dextrans, cross-linked agarose, etc. For instance, one may employ Sepharose ® 4B, or the like. The lectin is covalently bound to the matrix by means of cyanogen bromide or the like, using the method described by Cuatrecasas, *J. Biol. Chem.*, 1970, Vol. 245, pages 3059–3065. It should be noted that any method that covalently attaches a lectin to an insoluble matrix could be used to prepare the matrix of this invention.

Lectins are carbohydrate-binding proteins of nonimmune origin that agglutinate cells and/or precipitate complex carbohydrates and are isolated usually from seeds of plants. The preferred lectin for preparing the matrix for fractionating heparin is Concanavalin A. However, other D-mannose(D-glucose)-binding lectins may be used such as, for example, those described by Goldstein et al, in *Advances in Carbohydrate Chemistry and Biochemistry,* 1978, Vol. 35, pages 334–335.

The lectin-containing, water-insoluble matrix is mixed with antithrombin which becomes reversibly bound to the matrix, particularly to the lectin on the matrix. In a preliminary step, which is optional although preferred, the lectin-containing, water-insoluble matrix is equilibrated in an appropriate buffer generally characterized as the same buffer solution as that used hereinafter in which a mixture of antithrombin and heparin is applied to the matrix. This buffer contains sodium chloride at a level no greater than 0.25 M, preferably at physiological concentration (0.15 M), and has a pH in the range of 6 to 8.5. The equilibration is carried out for a period of about 0.1–2 hours at a temperature of about 5°–30° C.

After the lectin-containing, water-insoluble matrix is equilibrated, it is mixed with antithrombin, either pure or a mixture with other proteins that will not bind to the lectin, together with an excess of heparin, in an amount such that the resultant system will fractionate heparin into high and low activity fractions. Usually, about 50–1000 parts of matrix are mixed with one part of antithrombin. By an excess of heparin is meant that about 1–100 parts, preferably 4–20 parts, of unfractionated heparin are employed per part of antithrombin.

The mixture of antithrombin, heparin, and the lectin-containing, water-insoluble matrix is held in contact for a period of time and at a temperature sufficient to allow the antithrombin to bind to the lectin portion of the matrix. During that time the HAH becomes complexed to the antithrombin. Thus, the mixture of antithrombin, heparin, and the matrix are held for a period of about 0.1–2 hours at a temperature compatible with the system, usually at a temperature of about 5°–30° C. Generally, the antithrombin and heparin are in solution in an appropriate buffer, preferably, the buffering system employed in the above-described equilibration of the lectin-containing, water-insoluble matrix; and the solution is applied to a bed or column of the lectin-containing matrix.

Next, the matrix is washed to remove unbound heparin. The wash solution should contain a physiologically acceptable salt having an ionic strength sufficient to remove all unbound heparin from the matrix but insufficient to remove HAH or the antithrombin-HAH complex, preferably an ionic strength of about 0.1–0.4. The pH of the wash solution should be about 6.0–8.5.

A suitable aqueous solution in accordance with this aspect of the invention is, by way of example and not limitation, 0.1–0.4 M sodium chloride (ionic strength=0.1–0.4) at pH 6.0–8.5. Ionic strengths less than 0.1 should be avoided. Low ionic strength promotes non-specific interactions between the lectin and heparin itself. Low temperatures are to be avoided since such temperatures also promote the above interactions. Thus, the preparation of the complex should be conducted at a temperature greater than 5° C., preferably within the temperature range 20°–30° C., and no greater than 37° C. In general, the temperature and ionic strength should be adjusted to achieve the appropriate binding needed for selective complex formation where higher temperatures require lower ionic strengths within the above ranges.

In general, the matrix is washed until no unbound heparin appears in the wash solution as determined by known methods. The wash solution is rich in LAH.

The matrix, having been stripped of unbound heparin as described above, but containing antithrombin and HAH reversibly bound thereto, may be treated to separate HAH free of antithrombin. To this end the matrix is treated with an aqueous solution containing a physiologically-acceptable salt having an ionic strength sufficient to elute the adsorbed HAH but insufficient to remove other bound proteins, if any. For this purpose the ionic strength of the aqueous solution should be greater than 0.5, preferably 1, and within the range of about 0.5–2 M. The pH of this eluting solution should be about 6.0–8.5. It is preferred that the eluting solution should contain the same physiologically acceptable salt as the aforementioned wash solution for removing unbound heparin. A preferred eluting solution, then, is 0.5–2 M sodium chloride (ionic strength=0.5–2) at pH 6.0–8.5. The matrix is eluted until the adsorbed HAH has been removed therefrom as evidenced by the absence of HAH in the eluting solution. The presence of HAH in the eluting solution may be determined by conventional means.

The eluate containing HAH is treated to reduce its water content and to reduce the concentration of salt in the eluate, to a physiologically acceptable level, i.e., to 0.15 M or less. The aforementioned objective may be accomplished, for example, by dialysis against an aqueous sodium chloride-buffer solution in final container concentration, i.e., the concentration of the above as found in the final container as the product generally is sold and/or used. Generally, the final container concentration of sodium chloride is about 0.15 or less. Other means of achieving removal of the salt will be suggested to those skilled in the art. The HAH solution can be buffered to achieve physiological pH, filtered, and sterile filtered prior to water removal. It is noteworthy that heparin solutions, including solutions of HAH and LAH prepared in accordance with this invention, are sterilizable by boiling and also rendered non-hepatitis-infective thereby.

HAH concentrates can be formulated into pharmaceutical preparations. The term "pharmaceutical preparation" is intended in a broad sense herein to include preparations used for therapeutic purposes, for diagnostic purposes, for tissue culture purposes, and so forth. The pharmaceutical preparation intended for therapeutic use should contain a therapeutic amount of HAH, i.e., that amount necessary for preventative or curative health measures. If the pharmaceutical preparation is to be employed as a reagent, then it should contain reagent amounts of HAH. Similarly, when used in tissue culture or as a culture medium the pharmaceutical preparation should contain an amount of HAH sufficient to obtain the desired growth. It is a characteristic of compositions comprising high activity heparin prepared in accordance with the present invention that they contain HAH in pharmaceutically useful amounts. As mentioned earlier, high activity heparin has been prepared only in the laboratory scale production of heparin by gel chromatography; consequently, compositions containing HAH in pharmaceutically useful amounts have, heretofore, been unknown. Furthermore, in the above heparin preparation using gel chromatography, the heparin necessarily had to be fractionated by size prior to use; and only fractionated-by-weight heparin was employed. The molecular weight of the high activity heparin in the present HAH is representative of non-fractionated-by-size heparin, i.e., derived from the heparin not previously fractionated by size. It is also noteworthy that the instant HAH is essentially free of low activity heparin, and the activity of the high activity heparin is greater than about 300 U/mg, usually within the range of about 400–750 U/mg.

To prepare them for intravenous administration the compositions are constituted usually in water containing physiologically compatible substances such as sodium chloride, glycine, sugar and the like in physiologically compatible concentrations and having a buffered pH compatible with physiological conditions. Generally, guidelines for intravenously administered compositions are established by governmental regulations.

For anticoagulant purposes HAH prepared in accordance with this invention is expected to be a more potent agent and more predictable in dose-response than unfractionated heparin. In addition, the instant HAH should have fewer of the side effects currently associated with the clinical use of unfractionated heparin in the large dosages required.

LAH concentrates can be prepared from the aforedescribed wash solutions (wherein unbound heparin was separated from the matrix) in a manner similar to that outlined above for the HAH. The so-prepared concentrates may be formulated into pharmaceutical preparations.

After elution of LAH and HAH from the matrix, the matrix can be treated to remove antithrombin therefrom by contacting the matrix with a solution of a carbohydrate having the ability to displace antithrombin from the matrix. Usually, the amount and type of carbohydrate necessary and the pH of the solution should be sufficient to cause separation of the antithrombin from the matrix. Generally, about 0.02–0.5 M aqueous solution of carbohydrate at pH 6–8.5 is applied until the antithrombin is removed from the matrix. As the carbohydrate one may use those carbohydrates disclosed by Goldstein et al, supra, such as glucopyranosides, mannopyranosides, and fructofuranosides. Mono- and disaccharides also may be employed to separate the complex from the matrix and are preferred in this particular step. Thus, one may use, by way of example and not limitation, glucose, maltose, mannose, galactose, fructose, lactose, sucrose, and the like. It is within the compass of the invention to employ sugar alcohols such an mannitol, sorbitol, and the like to isolate the aforementioned complex. The eluted antithrombin solution is treated to remove carbohydrate therefrom by conventional means such as dialysis, etc., and then processed to put it into condition for use.

It is also within the scope of the invention to initially reversibly immobilize, in the absence of heparin, antithrombin on the equilibrated lectin-containing, water-insoluble matrix from above and use the resulting matrix to fractionate heparin. Thus, the matrix may be mixed with antithrombin, either pure or in a mixture of other proteins that will not bind to the lectin on the matrix, in an amount such that the resulting system will fractionate heparin into high and low activity fractions. About 50–1000 parts of matrix are mixed usually with one part of antithrombin. The reaction conditions for binding antithrombin to the matrix are the same as those described above when heparin is present.

In situations where the antithrombin solution (in an appropriate buffer system as described above) is not applied to a bed or column of matrix, the matrix with bound antithrombin is treated to separate it from the antithrombin solution. This may be accomplished by techniques known in the art such as filtration, decantation, and the like.

Next, the matrix is washed to remove residual antithrombin solution and impurities not bound to the matrix. Preferably, the wash solution is the same buffer solution described above in the equilibration step.

It is characteristic of the aforedescribed system that the antithrombin is bound reversibly thereto through the lectin on the matrix. The antithrombin is bound sufficiently to immobilize it but not great enough to cause the destruction of antithrombin upon its removal from the matrix. Thus, the antithrombin is non-destructively-removably bound to the lectin-containing matrix. The exact nature of this reversible binding is not known. However, hydrogen bonding and chargedipole interactions may be involved.

In the next step in this particular embodiment of the invention, heparin is contacted with the antithrombin-containing, lectin-containing, water-insoluble matrix onto containing, lectin-containing, water-insoluble matrix onto which the high activity heparin (HAH) is adsorbed. In general practice the unfractionated heparin is in the form of a solution in a buffer system containing sodium chloride in a concentration less than 0.4 M, usually about 0.1–0.4 M, and preferably at physiological concentration, i.e., 0.15 M. The pH of the buffer solution should be about 6.0–8.5, usually about 7.5. As the buffer solution one may use, for example, a mixture of 0.01 M TRIS (hydroxymethyl) aminoethane (TRIS) and 0.15 M sodium chloride. The amount of heparin mixed with the matrix should be sufficient to allow fractionation of the heparin to give HAH or LAH. The following relationship pertains: To maximize the activity of HAH obtained in the fractionation, no less than about 1 part, preferably 4–20 parts, of unfractionated heparin per part of antithrombin on the matrix is applied to the matrix. To minimize the activity of LAH obtained in the fractionation, about 0.05–0.25 parts of unfractionated heparin per part of antithrombin are applied to the matrix. The heparin may be in pure form or it may be mixed with other proteins and the like which do not bind to antithrombin in significant amounts. Generally, contact between the heparin solution and the matrix is achieved by forming a bed of freshly equilibrated matrix and passing the heparin solution therethrough.

LAH and HAH are gradiently eluted from the matrix by treating the matrix with the appropriate eluting solutions described earlier. After LAH and HAH are eluted separately from the matrix, antithrombin may be removed from the matrix as previously described. It is important to note that the antithrombin may be left on the lectin-containing matrix, and the matrix used repeatedly to fractionate heparin. Furthermore, the fractions of HAH and LAH obtained may be reapplied to the matrix for further purification.

It should be obvious, therefore, from the above discussion that if the fractionation of heparin is carried out for the purpose of securing the maximum activity in HAH, the unbound heparin will contain low activity heparin which does not represent the lowest activity possible. This results because of the large amount of unfractionated heparin that must be applied to the matrix relative to the antithrombin on the matrix. Thus, the so-recovered unbound heparin can be re-fractionated to minimize the activity of LAH.

It is within the purview of the invention to obtain antithrombin free of heparin using the lectin-containing, water-insoluble matrix described above. In this embodiment of the invention antithrombin contaminated with heparin is applied to the matrix, which then is treated with an aqueous salt solution as described above to elute HAH from the matrix. In this case all heparin species on the matrix are removed therefrom. Next, the matrix is treated with an aqueous carbohydrate solution as previously described to remove the antithrombin, which can be treated, if desired, to remove carbohydrate therefrom by conventional means such as dialysis, etc., and then processed to put it into condition for use. It should be clear from the above that the antithrombin contaminated with heparin may also be contaminated with other materials which do not bind to the matrix or which bind to the matrix and cannot be removed under conditions used for removing heparin or antithrombin from the matrix.

EXAMPLES

The invention is demonstrated further by the following illustrative examples.

Assay Methods

Antithrombin III. The Lowry protein assay was used using human serum albumin as the standard (Lowry et al, *J. Biol. Chem.*, 1951, Vol. 193, pages 265–275).

Heparin. Two assays were employed—

(a) Carbazole Assay: A quantitative assay for heparin based on a standard curve of uronic acid. A uronic acid content of 30% was assumed for heparin (Hook et al, *FEBS Letters*, 1976, Vol. 66, pages 90–93). The assay was described by Bitter et al, in Anal. *Biochemistry*, 1962, Vol. 4, pages 330–334.

(b) Azure A Method: A qualitative assay based on the method of Jacques et al, *J. Physiol.* (London), 1949, Vol. 109, pages 41–48, (see also Lam et al, BBRC, 1976, Vol. 69, pages 570–577).

Anticoagulant Activity of Heparin. The activity of all heparin fractions was related to that of a commercially obtained preparation (Lipo-Hepin®, Riker Laboratories, Inc.) whose U.S.P. unitage was defined on the label. A standard curve was established with the above heparin, and all heparin fractions of unknown activity were determined by comparison to this curve by the following scheme:

(1) a 200 µl sample containing antithrombin (approximately 30 µg/ml) and 200 µl of a heparin-containing solution were combined and warmed to 37°.

(2) A 200 µl sample of a solution containing thrombin (Pentex® bovine thrombin, Miles Laboratories, Inc.) at a level in excess of the antithrombin was added to the mixture of (1) above and rapidly mixed.

(3) After exactly 30 seconds, 200 µl of a solution of 1 mM S-2238 (H-D-Phe-L-Pip-L-arg-p-nitroanilide, Kabi Diagnostica, Sweden) and 0.5 mg Polybrene® (Aldrich Chemical Co., Inc.) was added to the mixture which was again rapidly mixed.

(4) After exactly 60 seconds, 200 µl of 50% acetic acid was added to stop the esterolytic reaction.

(5) The U.V. absorbance of each sample was determined at 405 nanometers (nm).

EXAMPLE 1

Preparation of Antithrombin-Concanavalin A-Sepharose Support

A column (1.6×5 cm) was prepared from a 10 ml suspension of Concanavalin A-Sepharose (Pharmacia Corp., Piscataway, N.J.). This agarose gel contains 8 mg of the lectin protein covalently bound per ml of swollen gel as stated by the manufacturer. The column was equilibrated with a buffer containing 0.15 M NaCl and 0.01 M TRIS, pH 7.5. (Optionally, this buffer solution can include agents to prevent bacterial growth, e.g., sodium azide 0.02% and other salts which stabilize Concanavalin A, namely, 0.1 mM calcium chloride and 0.1 mM manganese chloride, which are not otherwise essential for the experiments to be described).

A solution containing antithrombin (0.83 mg/ml) in the above buffer was applied to the column. Protein which was not bound to the column was monitored by ultraviolet (UV) spectioscopy at 280 nm. An unbound protein fraction was found to contain 1.13 mg which represents approximately 9% of the applied material (12.5 mg). Thus, approximately 11.4 mg of antithrombin was bound by the Concanavalin A-Sepharose, which is approximately 1.4 mg antithrombin per mg of Concanavalin A lectin.

EXAMPLE 2

Fractionation of Heparin to Produce HAH

To a column similar to that described in Example 1 was applied heparin (85 mgs) dissolved in 10 ml of a buffer containing 0.01 M TRIS, pH 7.5, and 0.15 M NaCl. The column was eluted with the above buffer until no further heparin was detectable in the eluate as described previously.

The column was eluted next with an aqueous buffer solution containing 1 M NaCl and 0.01 M TRIS at pH 7.5. The presence of HAH in the eluate was monitored by the Azure A Method. Fractions containing HAH were pooled and dialyzed to reduce the concentration of NaCl. The HAH contained in this eluate possessed a specific anticoagulant activity of 406 units/mg.

No antithrombin was found in the 1 M NaCl eluate, thus, it remained bound to the column, which was reequilibrated to the starting conditions with a buffer containing 0.01 M TRIS, pH 7.5, 0.15 M NaCl in preparation for further use.

Essentially similar results were observed for 6 repeated fractionations according to the above procedure.

Heparin containing eluates, as well as the starting material, were analyzed by the carbazole assay and for anticoagulant activity and are summarized in Table 1.

TABLE 1

| | Amount of heparin (mg) | Activity (Units) | (Units/mg) |
|---|---|---|---|
| Applied sample | 85.3 | 13,220 | 155 |
| Unbound fraction | 75.3 | — | — |
| Bound fraction (HAH) | 0.94 | 380 | 406 |

EXAMPLE 3

Fractionation of Heparin to Produce LAH

The fractionation of heparin to produce LAH is carried out in a similar manner to that for producing HAH described in Example 3 with the exception that a much smaller amount of unfractionated heparin is applied to the column. In the present case, 3.4 mg of heparin was applied to a column prepared as described in Example 1. This heparin was dissolved in a buffer containing 0.01 M TRIS, pH 7.5, and 0.15 M NaCl. The column was eluted with this buffer until no further heparin was detectable in the eluate by the Azure A Method. The LAH contained in this unbound heparin fraction was of very low activity, possessing a specific anticoagulant activity of only 4.3 units/mg.

Further elution of this column with buffer containing 1 M NaCl resulted in the elution of a moderately high activity heparin material, possessing a specific activity of 259 units/mg. All heparin-containing eluates were assayed by the carbazole assay and for anticoagulant activity as summarized in Table 2.

This column was re-equilibrated to starting conditions as described in Example 2.

TABLE 2

|  | Amount of heparin (mg) | Activity (Units) | (Units/mg) |
|---|---|---|---|
| Applied sample | 3.44 | 544 | 158 |
| Unbound fraction (LAH) | 1.49 | 6.4 | 4.3 |
| Bound fraction (HAH) | 1.32 | 342 | 259 |

EXAMPLE 4

Recovery of Reversible-immobilized Antithrombin from the Support

The re-equilibrated column of Example 4 was treated with a sufficient amount of an aqueous buffer solution containing 0.2 M 1-0-methyl-α-D-glucopyranoside to remove antithrombin. Removal of antithrombin from the column as monitored by UV absorption at 280 nm; 8.63 mg (76% of that originally estimated to be bound to the column in Example 1) was recovered. The sugar was removed from the anti-thrombin-containing eluate by dialysis against a buffer containing 0.01 M TRIS, pH 7.5, and 0.15 M NaCl.

I claim:

1. A composition for fractionating heparin into components of differing activity by virtue of differing affinity for antithrombin, which comprises a lectin-containing, water-insoluble gel matrix having reversibly bound thereto antithrombin specific for gradiently binding the components of differing activity in heparin.

2. The composition of claim 1 which contains an amount of antithrombin sufficient to gradiently bind the components of differing activity.

3. The composition of claim 1 wherein the lectin is Concanavalin A.

4. The composition of claim 1 wherein the water-insoluble gel matrix is an agarose gel.

5. The composition of claim 1 wherein the heparin is unfractionated heparin.

* * * * *